US008684961B2

(12) United States Patent
Gottenbos et al.

(10) Patent No.: US 8,684,961 B2
(45) Date of Patent: Apr. 1, 2014

(54) INSERT FOR A BREAST PUMP

(75) Inventors: Bart Gottenbos, Budel (NL); Rachel Estelle Thilwind, Cambridge (GB); Jozef Johannes Maria Janssen, Herten (NL); Marjolein Irene Van Lieshout, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/377,303

(22) PCT Filed: Jun. 9, 2010

(86) PCT No.: PCT/IB2010/052563
§ 371 (c)(1),
(2), (4) Date: Dec. 9, 2011

(87) PCT Pub. No.: WO2010/146501
PCT Pub. Date: Dec. 23, 2010

(65) Prior Publication Data
US 2012/0083731 A1 Apr. 5, 2012

(30) Foreign Application Priority Data
Jun. 18, 2009 (EP) .................................. 09163034

(51) Int. Cl.
*A61M 1/06* (2006.01)
(52) U.S. Cl.
USPC .............................................. 604/74; 604/73
(58) Field of Classification Search
USPC .................................................... 604/73–75
See application file for complete search history.

(56) References Cited

U.S. PATENT DOCUMENTS

| 2,542,505 | A | 2/1951 | Gascoigne |
| 4,263,912 | A | 4/1981 | Adams |
| 4,323,067 | A | 4/1982 | Adams |
| 6,579,258 | B1 * | 6/2003 | Atkin et al. ..................... 604/74 |
| 7,396,340 | B2 | 7/2008 | Onuki et al. |
| 2005/0171471 | A1 | 8/2005 | Morton et al. |
| 2005/0234370 | A1 | 10/2005 | Beal et al. |
| 2006/0270973 | A1 | 11/2006 | Chu |
| 2007/0088250 | A1 | 4/2007 | Silver et al. |
| 2007/0161948 | A1 | 7/2007 | Renz et al. |
| 2012/0004604 | A1 * | 1/2012 | Van Der Kamp et al. ...... 604/74 |

FOREIGN PATENT DOCUMENTS

| CA | 02240268 A1 | 12/1999 |
| EP | 1593402 A1 | 11/2005 |
| EP | 1593402 B1 | 7/2008 |

* cited by examiner

Primary Examiner — Nicholas Lucchesi
Assistant Examiner — Benjamin Koo

(57) ABSTRACT

An insert for a breast-receiving funnel of a breast pump includes an elongate inflatable bladder which defines a pressure chamber. The elongate inflatable bladder is configured to fit in a teat receiving space of the breast receiving funnel so that the bladder extends from an inner end of the funnel towards an outer end of the funnel. The bladder lies between a user's teat and the funnel when a breast is inserted in the funnel, such that the elongate inflatable bladder is configured to deform towards a user's teat located in the teat receiving space in a predetermined manner when a pressure difference is applied between the teat receiving space and the pressure chamber such that a peristaltic action is applied to the user's teat, to aid the expression of milk therefrom.

13 Claims, 2 Drawing Sheets

INSERT FOR A BREAST PUMP

FIELD OF THE INVENTION

The present invention relates to an insert for a breast pump. In particular, the present invention relates to an insert adapted to fit in a breast-receiving funnel of a breast pump which is operable to extract milk from a user. The present invention also relates to a breast-receiving funnel for a breast pump and a breast pump comprising a breast-receiving funnel.

BACKGROUND OF THE INVENTION

Breast pumps are well known devices for extracting milk from the breast of a user. A breast pump may be used if the baby is not itself able to extract the milk, or if the mother is separated from the baby, for example if away from the baby at work. The use of a breast pump to extract milk may also be used to stimulate and increase milk production in women with a low milk supply.

Conventional breast pumps make use of a vacuum to induce milk extraction from a nursing mother's breast. The pumping action of the device draws the milk from the nipple to a collection vessel, and the pressure and/or frequency may be adjusted to the preferences of the mother. Therefore, the adjustability of the breast pump to the preference of the mother is limited.

A conventional breast pump for extracting milk from a user's breast is shown in FIG. 1. Such a conventional breast pump unit 1 comprises a main body 2 and a feeding bottle 3. The feeding bottle 3 is attached to the main body 2 by a screw fitting.

A vacuum pump unit (not shown) is formed in the main body 2 to create a vacuum, as will be described hereinafter and a handle 4 extends from the main body 2. Breast pumps may be manually operated, for example by squeezing the handle or by operation of a foot pedal. Breast pumps may also be electrically driven by a small electric motor.

A breast-receiving funnel 5 is fixedly attached to the main body 2 for receiving the breast of a user. The funnel 5 comprises a mouth 6 and a throat 7. The mouth 6 is open at an outer end and an inner surface of the mouth 6 converges from the outer end towards the throat 7 to form a hollow recess. An insert 8 is insertable in the mouth 6 of the funnel 5 in an attempt to improve a user's comfort and aid the expression of milk. Such an insert is known from EP 1 593 402, in which an insert has a circle symmetric flexible membrane extending around an inner portion of a mouth of a funnel of a breast pump from the outer end to the throat of the funnel. The membrane is deformable into the hollow recess during use to apply a compressive force to the nipple and/or areola in an attempt to aid the expression of milk from the breast.

However, a problem with the breast pump described above is that users are known to suffer from discomfort or difficulty when using such a breast pump. When an infant feeds from its mother's breast, the baby applies two actions to obtain milk, a sucking action and a peristaltic movement created by the action of the infant's tongue on the nipple and areola of the mother's breast. The sucking action applies a negative pressure to latch onto the breast and induce milk flow. The infant can also perform a peristaltic tongue motion over the areola and nipple to induce milk flow from the breast. In this motion a rhythmic contraction and expansion motion is performed to induce the milk flow.

The peristaltic tongue motion stimulates the hormone-production responsible for the 'let-down' reflex which allows milk produced in the milk glands to be released into the milk ducts. Conventional breast pumps do not produce this peristaltic motion, and so the absence of such an action means that extracting milk can be uncomfortable and inefficient.

In an attempt to deal with these problems, a breast pump is disclosed in U.S. Pat. No. 4,263,912 which attempts to apply a peristaltic motion to a breast. The breast pump disclosed in this document has a circle symmetric flexible membrane with a varying thickness of membrane which increases from an outer end to an inner end of the mouth of the funnel so that the membrane is urged to deform into a nipple receiving space during use in a predetermined peristaltic manner, starting at the outer end of the funnel and deforming towards the inner end, proximate to a nipple end of the breast received in the funnel.

However, disadvantages of the above breast pump arrangement include the breast pump having a complicated construction and it is difficult to achieve a satisfactory peristaltic motion which is analogous to the action of a suckling infant.

SUMMARY OF THE INVENTION

Therefore, it is an object of the invention to provide a breast pump which substantially alleviates or overcomes the problems mentioned above and aids the expression of breast milk from a breast in a way that is more analogous to the action of a suckling infant.

According to the present invention, there is provided an insert for a breast-receiving funnel of a breast pump comprising an elongate inflatable bladder which defines a pressure chamber, the elongate inflatable bladder being adapted to fit in a teat receiving space of said breast receiving funnel so that the bladder extends from an inner end of said funnel towards an outer end of said funnel, and lie between a user's teat and the funnel when a breast is inserted in the funnel, such that the elongate inflatable bladder is configured to deform towards a user's teat located in the teat receiving space in a predetermined manner when a pressure difference is applied between the teat receiving space and the pressure chamber such that a peristaltic action is applied to said user's teat, to aid the expression of milk therefrom.

Preferably, the resiliently deformable membrane is configured to deform towards a user's teat located in the teat receiving space in a predetermined manner when a positive pressure is applied in the elongate inflatable bladder such that a peristaltic action is applied to a user's teat.

Conveniently, the elongate inflatable bladder is formed from a resiliently deformable membrane.

In one embodiment, the stiffness of the resiliently deformable membrane varies along the length of the bladder, such that the resiliently deformable membrane proximate to a front end of said bladder is lower than the stiffness of the resiliently deformable membrane at a distal rear end of said bladder.

In a preferred embodiment, the resiliently deformable membrane has a diverging wall thickness which increases away from said front end such that a thinner portion of said membrane proximate to the front end of the bladder deforms towards said user's teat located in said teat receiving space prior to a thicker portion of said membrane proximate to the rear end of the bladder deforms towards said user's teat.

Advantageously, the elongate inflatable bladder has a fluid inlet disposed proximate to said rear end of the bladder to allow the flow of fluid into and out of the pressure chamber.

Preferably, the resiliently deformable membrane forms opposing upper and lower membrane walls, wherein the lower membrane wall is configured to lie against the funnel and the upper membrane wall is configured to deform towards a user's teat located in the teat receiving space when the insert is disposed in said funnel.

The resiliently deformable membrane may be formed from a polymeric, non-elastomer material.

According to another aspect of the present invention, there is provided breast receiving funnel for a breast pump comprising an insert with an elongate inflatable bladder which defines a pressure chamber, the elongate inflatable bladder being adapted to fit in a teat receiving space of said breast receiving funnel so that the bladder extends from an inner section of said funnel to an outer section of said funnel, and lie between a user's teat and the funnel when a breast is inserted in the funnel, such that the elongate inflatable bladder is configured to deform towards a user's teat located in the teat receiving space in a predetermined manner when a pressure difference is applied between the teat receiving space and the pressure chamber such that a peristaltic action is applied to a user's teat, to aid the expression of milk therefrom.

A breast receiving funnel may further comprise a rigid outer shell with an opening for receiving a user's teat therethrough, wherein the insert locates against the rigid shell.

Preferably, the rigid outer shell comprises a planar inner surface and the insert locates against said planar inner surface.

Advantageously, the rear end of the bladder is disposed distal to the funnel opening and the front end of the bladder is disposed proximate to the funnel opening.

Conveniently, the bladder is mounted in the funnel at the rear end of the bladder such that the front end of the bladder is not constrained.

The funnel may comprise a mouth section and a throat section, the mouth portion including an opening to the funnel and the throat section connecting the mouth section to a main body of a breast pump, wherein the bladder is disposed in the throat section, and the front end of the bladder extends into the mouth section.

Preferably, the insert is a primary insert and the breast receiving funnel further comprises a secondary insert with a circumferentially extending resiliently deformable wall disposed in the mouth section and extends over the front end of the bladder such that said front end does not contact a user's teat when a user's teat is disposed in said funnel.

In one embodiment, a portion of the secondary insert extends into the throat section of the funnel and said section is diametrically opposite and circumferentially spaced from the primary insert in said throat.

The insert may be removably mounted to the funnel.

According to yet another aspect of the invention, there is provided a breast pump including a breast receiving funnel with an insert comprising an elongate inflatable bladder which defines a pressure chamber, the elongate inflatable bladder being adapted to fit in a teat receiving space of said breast receiving funnel so that the bladder extends from an inner end of said funnel towards an outer end of said funnel, and lie between a user's teat and the funnel when a breast is inserted in the funnel, such that the elongate inflatable bladder is configured to deform towards a user's teat located in the teat receiving space in a predetermined manner when a pressure difference is applied between the teat receiving space and the pressure chamber such that a peristaltic action is applied to said user's teat, to aid the expression of milk therefrom.

Preferably, the breast pump includes means for generating a positive pressure in the insert.

BRIEF DESCRIPTION OF THE DRAWINGS

Preferred embodiments of the invention will now be described, by way of example only, with reference to the accompanying drawings, in which.

DETAILED DESCRIPTION OF THE EMBODIMENTS

Figure 1:
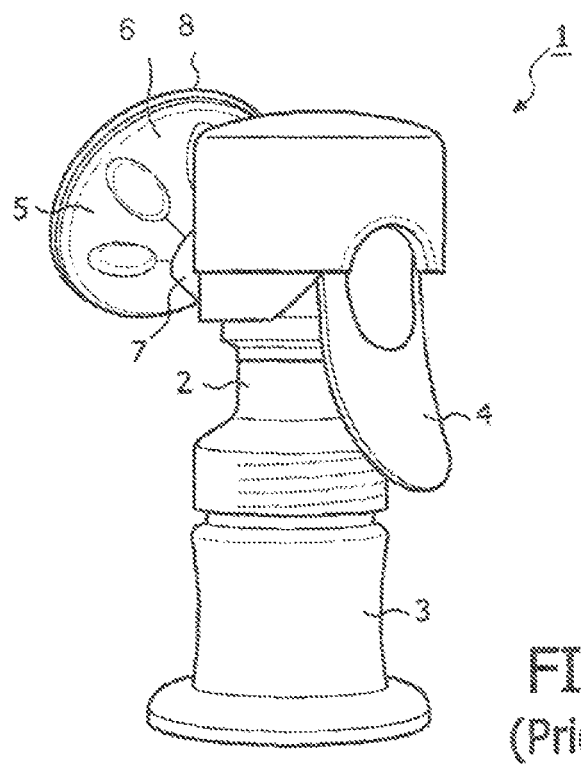
FIG. 1 illustrates a perspective view of an existing breast pump.
Figure 2:
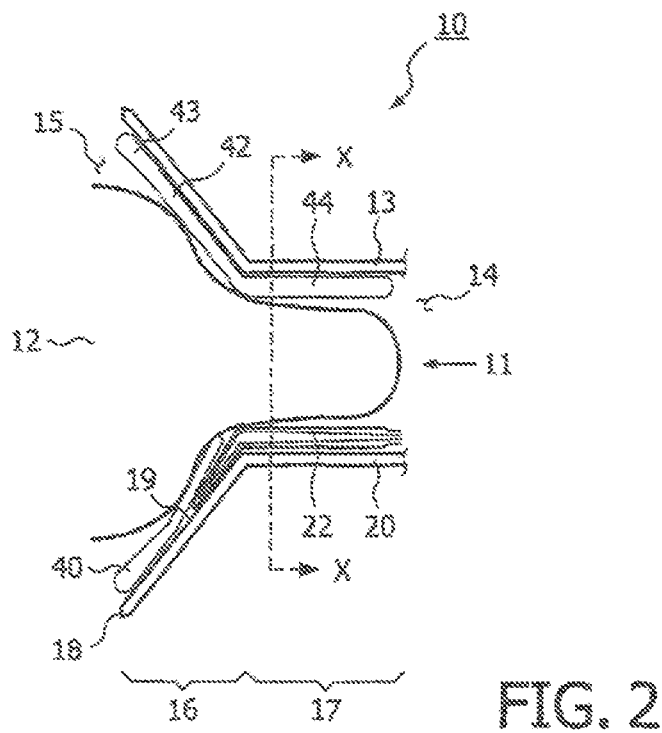
FIG. 2 illustrates a cross-sectional side view of a breast receiving funnel and an insert for a breast pump according to a first embodiment of the present invention.
Figure 3:
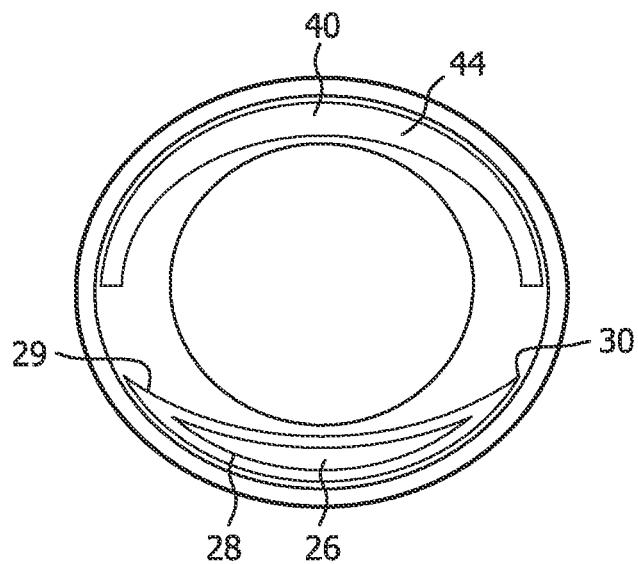
FIG. 3 illustrates a schematic cross-sectional side view of the breast receiving funnel and insert shown in FIG. 2 along the line X-X.

Referring now to FIGS. 2 and 3, a breast receiving funnel 10 for a breast pump unit is shown. The breast pump unit (not shown) comprises a main body and a milk-receiving vessel. The milk receiving vessel, which may take the form of a feeding bottle for an infant or baby, is attached to the main body by a screw fitting, although it will be understood that alternative releasable attachment means may be used, such as clips (not shown).

A vacuum pump unit (not shown) is disposed in the main body, to create a vacuum, as will be described hereinafter and a handle (not shown) extends from the main body. The vacuum pump unit is motorised and the handle operates a motorised vacuum pump unit (not shown) which is powered by batteries disposed in the main body. Alternatively, the handle is manually operable to operate the vacuum pump unit. The vacuum pump unit is conventional and so no further description of the pump unit will be given here.

The breast receiving funnel 10 extends from the main body (not shown) of the breast pump (not shown) and has a hollow recess for receiving the breast of a user 12. The funnel 10 comprises an outer shell 13. The outer shell 13 extends from the main body (not shown) and is integrally formed therewith. The outer shell 13 defines a passageway which communicates with the vacuum pump unit at an inner end 14 of the funnel 10, proximal to the main body, and has an opening 15 at an outer end 18 of the funnel 10, distal to the main body.

The breast receiving funnel 10 comprises a mouth section 16 and a throat section 17. The mouth section 16 is conical and forms the opening 15 at the outer end 18. An inner surface 19 of the mouth section 16 converges from the outer end 18 towards the throat section 17. The throat section 17 is tubular with a circumferentially extending inner surface 20 and extends between the mouth section 16 and the breast pump main body. The mouth section 16 and throat section 17 are formed by the outer shell 13 and are integrally formed with each other and main body. The outer shell 13 is formed from a rigid, non-deformable material, such as a rigid plastic for ease of manufacture and to allow sterilisation, although alternative suitable materials may be used.

Although in the present embodiment the outer shell 13 of the funnel 10 is integrally formed with the main body (not shown) of the breast pump, it will be understood that in an alternative embodiment the funnel 10 is removably mounted thereto. Such a funnel 10 is removably mounted to the main body of the breast pump to aid cleaning or sterilisation of the funnel 10 and main body.

The mouth and throat sections 16,17 of the funnel 10 together define a teat receiving space 11 and a fluid passageway is provided between the teat receiving space 11 of the funnel 10 and the milk receiving vessel (not shown), through the main body. The fluid passageway also enables the vacuum pump unit (not shown) disposed in the main body (not shown) to create a negative pressure in the teat receiving space of the funnel 10 when a user's breast is disposed therein, as will be explained below. The mouth section inner surface 19 and the throat section inner surface 20 together define a funnel inner surface.

Figure 4:
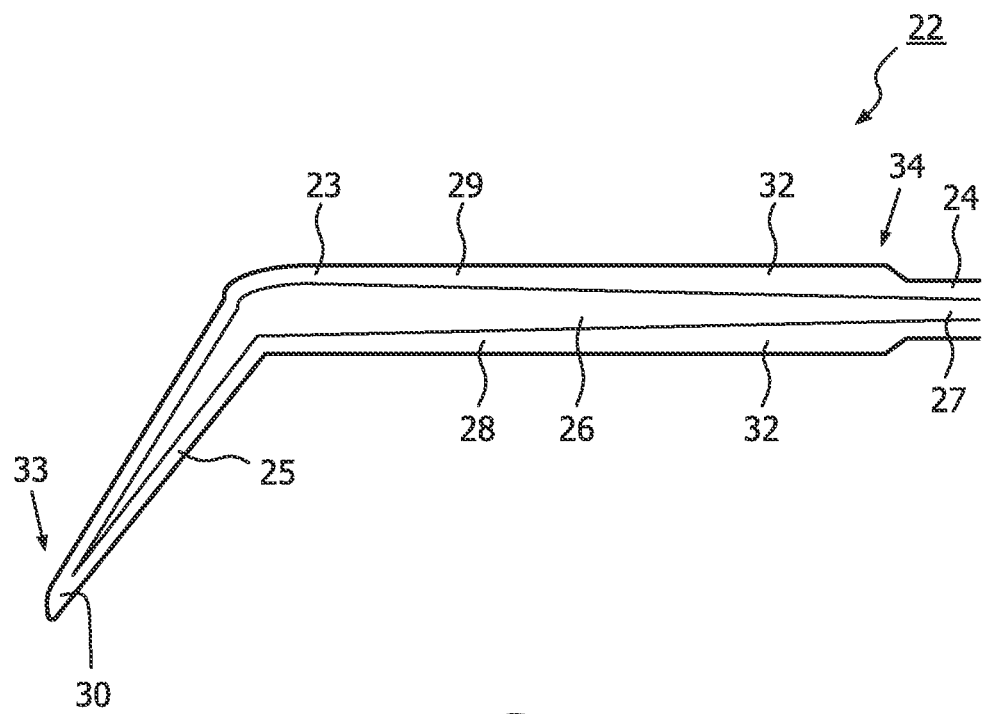
FIG. 4 illustrates a cross-sectional side view of the insert for a breast pump shown in FIG. 3.

A primary insert 22 is shown in FIGS. 2 to 4 and is adapted to fit in the breast-receiving funnel 10 of the breast pump unit. The primary insert 22 comprises an elongate inflatable bladder 23 and a fluid inlet 24. The elongate inflatable bladder 23 is formed as a flat cushion with an outer membrane 25 and a pressure chamber 26 defined by the outer membrane 25. The fluid inlet 24 extends from one end of the inflatable bladder 23 and forms a hollow tube 27 which communicates between the pressure chamber 26 and a pressure generating means (not shown). It will be understood that the shape of the connection 27 is of minor importance, as long as it is fluid tight and can cross the distance to the pressure source.

The pressure generating means can be simply a connection to the outside air, in essence keeping the pressure chamber 26 at atmospheric pressure. In order to increase the compressive force of the inflatable bladder 23 on the teat a truly pressure generating means can be added to the pump unit (not shown), elevating the pressure in the pressure chamber 26 above atmospheric levels.

The elongate inflatable bladder 23 is generally tongue shaped, that is in a deflated state the bladder has a lower membrane wall 28, an opposing upper membrane wall 29 and a peripheral membrane edge 30 conjoining the lower and upper membrane walls 28,29 and extending therearound along a pair of opposing sides 32, a front end 33 and a rear end 34. The fluid inlet 24 extends from the rear end 34 of the bladder 23.

The outer membrane 25 is resiliently deformable and has a wall thickness which varies from its front end 33 to its rear end 34. An inner surface of each of the lower and upper membrane walls 28,29 and a corresponding outer surface of each of the lower and upper membrane walls 28,29 diverge away from each other from the bladder front end 33 to the bladder rear end 34, and so as the wall thickness of the outer membrane 25 increases the stiffness of the outer membrane 25 is increased, such that the outer membrane is less deformable towards its rear end 34.

The inflatable bladder 23 is formed from a polymeric non-elastomer material, for example polyurethane, polypropylene or polyethylene, although it will be understood that the material is not limited thereto and that any suitable material may be used, for example an elastomer such as silicone rubber. In the above embodiment, the outer membrane 25 of the primary insert 22 has a matted surface structure, which has a low friction resistance.

The primary insert 22 is removably disposable in the funnel 10. In this exemplary embodiment, the primary insert 22 is disposed primarily in the throat section 17 with a portion extending into the mouth section 16. It will be understood that in an alternative embodiment the primary insert 22 is disposed in the mouth section 16 of the breast receiving funnel 10 dependent on the shape of the funnel and the positioning of a user's breast therein.

The lower membrane wall 28 locates against the funnel inner surface on a lower region thereof, when the breast pump is held in its operable position with the milk-receiving vessel (not shown) lowermost. As shown in FIG. 2, the main portion of the bladder 23 is disposed in the throat section 17 lying against a portion of the throat section inner surface 20 and a front portion of the bladder 23 proximate the front end 33 flexes downwardly to locate against the mouth section inner surface 19. In a preferred embodiment the throat inner surface 20 and the mouth section inner surface 19 have planer sections (not shown) against which the lower membrane wall 28 locates, however the mouth and throat inner surfaces 19,20, against which the lower membrane wall 28 locates may be curved, as shown in FIG. 3.

The primary insert 22 is removably insertable in the funnel 10 to aid cleaning and sterilisation, although it will be appreciated that the insert may be fixedly mounted in the funnel. In this exemplary embodiment, the primary insert 22 is mounted in the funnel 10 by the fluid inlet 24 fixedly connecting to a connection mount (not shown). The connection mount (not shown) provides a fluid passageway to a positive pressure producing means (not shown) or to ambient pressure, as will become apparent hereinafter, such that a pressure difference can be produced between the teat receiving space 11 and the pressure chamber 26 of the elongate inflatable bladder 23 by air flow through the fluid inlet 24 to inflate said bladder 23. An advantage of the above arrangement is that the primary insert 22 is able to slide freely over the inner surface of the funnel, and so is not constrained when the bladder 23 is inflated, and the lower and upper membrane walls 28,29 swell and the peripheral edge 30 is urged away from the inner surface of the funnel 10, as will become apparent hereinafter.

It will be understood that the primary insert 22 may be mounted to the funnel 10 by other means, however such a mounting means is disposed at the rear end of the insert, distal from the front end to allow the front end to be urged away from the inner surface of the funnel as the bladder is inflated, and spaced from the peripheral edge of the bladder to allow the lower membrane wall to swell outwardly when the bladder is inflated, as will become apparent hereinafter.

The breast pump further comprises a secondary insert 40 which is formed from a resiliently deformable material, such as a suitable rubber material, and is may be transparent to give the mother a view on the location of the teat.

The secondary insert 40 comprises an outer part 42 with a circumferentially extending, resiliently deformable wall 43 which converges inwardly to form a generally conical shape and is configured to lie against the mouth section inner surface 19. An arced inner part 44 extends from the narrow part of the outer part 42 and is configured to lie against the throat section inner surface 20 in an upper region thereof, when the breast pump is held in its operable position with the milk-receiving vessel (not shown) lowermost.

Operation of the breast pump and the primary insert 22 according to the above exemplary embodiment will now be described with reference to the drawings.

A user inserts the primary insert 22 into the throat section 17 of the funnel 12; the insert 23 being mounted therein by the fluid inlet 24 being attached to the connection mount (not shown). The lower membrane wall 28 locates against the inner surface of the funnel, with the bladder 23 flexing such that a portion locates against the mouth section inner surface 19.

The secondary insert 40 is then inserted into the mouth section 16 of the funnel 10, with the front end 33 of the bladder 23 being disposed between the inner surface 19 of the mouth section 16 and the resiliently deformable wall 43 of the secondary insert outer part 42. The arced inner part 44 extends into the throat section 17 of the funnel 10 and locates against the inner surface 20 of the throat section 17 spaced from and diametrically opposite the primary insert 22. Therefore, the primary insert 22 and secondary insert inner and outer part 42,44 define the teat receiving space 11 therebetween. A user's teat is inserted into the teat receiving space 11 during use of the breast pump, as will be explained in detail hereinafter.

An advantage of the above arrangement is that the primary insert 22 does not extend circumferentially around the outer shell 13 of the funnel 10 and so, in an embodiment wherein the outer shell 13 is transparent, it is possible for a user to see inside the funnel 10 through regions of the outer shell 13 defined between the primary insert 22 and the secondary insert 40, which are spaced from each other, and so view the user's teat and the expression of milk therefrom. In known peristaltic breast pumps, wherein the insert extends circumferentially around an inner surface of the funnel it is difficult for a user to view the teat disposed in the funnel and the expression of milk therefrom, especially when the surface is structured (matted) for reduced friction with the teat surface.

The connection mount (not shown) to which the primary insert fluid inlet 24 is mounted provides a fluid communication between the pressure chamber 26 defined by the bladder 23 and a pressure generating means (not shown), such as an air pump, to provide a positive pressure differential in the pressure chamber 26, as will be explained below.

Once the primary and secondary inserts 22, 40 are inserted in the breast receiving funnel 10, the breast pump is then in an assembled state and the user inserts a breast through the funnel opening 15 into the teat receiving space 11. The user's areola and/or breast is disposed in the conically-shaped hollow section formed by mouth section 16 of the funnel 10 and locates and seals against the secondary insert 40. Hence, the user's teat comprising the areola and nipple is disposed in the teat receiving space 11.

A negative pressure is formed in the teat receiving space 11 by operating the vacuum pump unit (not shown). The negative pressure helps to induce milk extraction from the user's breast in the manner of a conventional breast pump by applying a negative pressure to the teat, and helps to maintain the breast pump 1 in position relative to the breast even when little or no support is provided externally.

When a negative pressure is applied in the teat receiving space 11, the teat is extruded in the teat receiving space 11 such that a substantial portion of the surface of the teat disposed in the teat receiving space 11 is proximate to the upper membrane wall 29 of the bladder 23, between the primary insert 22 and the arced inner part 44 of the secondary insert 40.

As well as the negative pressure being applied in the teat receiving space 11, a positive pressure is formed in the pressure chamber 26 by the pressure generating means via the hollow tube 27 of the fluid inlet 24. The positive pressure formed in the pressure chamber 26 creates a pressure differential between the teat receiving space 11 and the pressure chamber 26.

Alternatively, the hollow tube 27 of the fluid inlet can be connected to the outside air, keeping the pressure chamber 26 at atmospheric pressure. When the negative pressure in the teat receiving space 11 is rising, the pressure differential between this space 11 and the pressure chamber 26 will rise giving a similar action of the bladder 23, explained below, as with the formerly described positive pressure generating means, albeit with a lower teat compressive force.

The pressure differential between the teat receiving space 11 and the pressure chamber 26 causes the bladder 23 to expand and the lower and upper membrane walls 28,29 to be urged to distend outwardly due to their resiliently deformable nature. The rigid outer shell 13 of the funnel prevents the primary insert 22 from distending outwardly. Therefore, the primary insert 22 is urged to distend inwardly into the teat receiving space 11. Due to the varying wall thickness of the lower and upper membrane walls 28,29, wherein the wall thickness increases from a thinner portion of each wall 28,29 proximate the bladder front end 33 to a thicker portion of each wall 28,29 proximate to the bladder rear end 34, the membrane walls 28,29 proximate to the bladder front end 33 have a low stiffness which increases towards the bladder rear end 34.

Therefore, as the pressure differential between the teat receiving space 11 and the pressure chamber 26 increases, the thinner portion of each resiliently deformable membrane wall 28,29 is caused to swell and distend outwardly, and the higher stiffness of the thicker portion of each resiliently deformable membrane wall 28,29 prevents said thicker portion from deforming initially. Subsequently, as the pressure difference increases, a greater portion of each resiliently deformable membrane wall 28,29 is progressively caused to deform and distend outwardly. Therefore, the primary insert 22 is urged into the teat receiving space 11 and the upper membrane wall 29 is urged against the user's teat disposed therein. Therefore, the primary insert 22 is caused to progressively distend inwardly and urge against the user's teat disposed therein proximate to one end of the teat receiving space 11 towards the other end thereof. The user's teat is then compressed between the primary and secondary inserts 22,40.

The progressive deformation of each resiliently deformable membrane wall 28,29 due to the varying thickness of each wall 28,29 as the pressure in the pressure chamber increases causes the primary insert 22 to impart a peristaltic action on a user's teat which promotes the expression of milk from a user's teat and is more analogous to an infant or baby compared with a conventional breast pump action. Furthermore, an advantage of the present invention is that the primary insert 22 is anatomically similar and has a similar shape and movement as a baby's tongue, and the inner part 44 of the secondary insert 40 is analogous to a baby's palate. Therefore, the natural feel of the breast pump is enhanced. Milk is expressed from the user's breast and is expelled from the funnel 10 through the passageway defined by the outer shell 13 of the funnel 10 into the main body of the breast pump and into the milk receiving vessel.

As the insert is a bladder with a lower and upper membrane wall 28,29, the insert does not need to be fixedly mounted to the funnel at its outer end to fixedly locate the insert and/or to form a pressure chamber between insert and the outer shell of the funnel in which a positive pressure can be generated to inflate the bladder. An advantage of the pressure chamber 26 being formed by the bladder 23 is that it prevents the insert from being mounted to the funnel 10 in an incorrect manner and so causing leakage and loss of function. Furthermore, in a conventional breast pump the deformation of the insert is hampered by attachment of the insert to an outer rim of the funnel. However, in the present arrangement, the insert is not constrained thereby. Additionally, this also allows predictability of deformation as material folds are not required to allow deformation at the front end of the insert.

As the resiliently deformable lower and upper membrane walls 28,29 are urged to distend outwardly, the front end 33 of the bladder 23 is urged to distend inwardly towards the inner end 14 of the funnel 10. Therefore, the front end 33 of the bladder 23 and corresponding portion of the upper membrane wall 29 is urged to slide relative to the user's breast disposed in the teat receiving space 11. However, the user's breast is located against the secondary insert 40, which extends over the front end 33 of the bladder 23 and so said front end 33 does not contact the user's breast and friction discomfort is prevented. Furthermore, as the bladder 23 is not fixedly mounted to the outer shell 13 of the funnel, the bladder 23 is not constrained and so is free to inflate without being restrained at the front end 33 of the bladder.

An advantage of the front end 33 of the bladder 23 not be constrained is that it aids the progressive deformation of the resiliently deformable membrane walls 28,29 by not restricting said deformation at the front end 33 of the bladder 23 and so said front end 33 can inflate prior to the deformation of the rest of the resiliently deformable membrane walls 28,29 to impart an improved peristaltic action on a user's teat which promotes the expression of milk from a user's teat and is more analogous to that of an infant or baby.

To cause the resiliently deformable wall 26 to distend inwardly into its original position away from a user's teat, the pressure in the teat receiving space 11 is reduced to reduce the pressure differential. Therefore, the resiliently deformable membrane 23 is urged to distend inwardly into its original position, away from the teat, due to the stiffness and resilient nature of the bladder. As the pressure differential is reduced, the thicker portion of each resiliently deformable membrane wall 28,29 returns to its original shape and position, prior to the thinner portion of each resiliently deformable membrane wall 28,29 returning to its original shape and position.

By cyclically generating a positive pressure difference between the pressure chamber 26 and the teat receiving space 11, a repeated peristaltic action is imparted on a user's teat disposed in the teat receiving space 11.

The insert 22 is removable from the funnel 10. An advantage of the insert 22 being removable from the funnel 10 is that the insert is easy to clean. Furthermore, due to the limited number of components of the insert, the insert and breast pump assembly is easy to assemble and simple to manufacture.

Although the breast pump is configured for use with primary and secondary inserts as described in detail above, it will be understood that in an alternative embodiment the primary insert may be used in a breast pump without a secondary insert.

An advantage of the secondary insert is that the front end of the bladder is urged to slide relative to the user's teat located in the teat receiving space when the bladder is being inflated due to the lower and upper membrane walls swelling when a positive pressure differential is applied in the pressure chamber. Therefore, the presence of the secondary insert, which is disposed between a users breast and the sliding front end of the bladder prevents a user's discomfort due to friction caused by the front end of the bladder sliding relative to the user's breast.

Although the variation in stiffness along the resiliently deformable membrane 23 in the above exemplary embodiment is formed by the variation in thickness of the resiliently deformable membrane 23, it will be understood the variation in thickness may be achieved by other means, for example a plurality of ribs extending longitudinally along the bladder and integrally formed therewith to provide local thickening so as to increase the stiffness of the wall therealong.

Although in the above embodiment the primary insert is not fixedly mounted to the funnel, in an alternative embodiment the lower surface of the bladder is fixedly mounted to the inner surface of the throat of the funnel at the inner end of the bladder, proximate to the inlet. In this embodiment, the lower surface is fixedly mounted at the inner end and distal from the peripheral edge so that the ends of the bladder can still become shorter along the peripheral edge when it is inflated.

Although in the above exemplary embodiments the primary insert is disposed in the throat of the funnel with a portion extending into the mouth of the funnel, it will be appreciated that in an alternative embodiment the primary insert is disposed primarily in the mouth of the funnel, or is disposed entirely in the mouth or the throat of the funnel. The location of the primary insert is dependent on the shape of the funnel and the positioning of a user's teat therein when a user's breast is disposed therein such that a peristaltic action is applied to said user's teat, to aid the expression of milk therefrom. For example, if the funnel is shaped such that the teat is disposed entirely in the mouth of the funnel, and the user's teat does not extend into the throat of the funnel during use, then the primary insert will not be disposed in the throat of funnel.

Although in the above exemplary embodiments the primary insert is inflated by means of air, it will be understood that the primary insert may be inflated by alternative fluids flowing into the pressure chamber, which includes a gas or a liquid.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claims in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. An insert for a breast receiving funnel of a breast pump comprising:
   a primary insert portion having an elongate inflatable bladder which defines a pressure chamber; and
   a secondary insert portion having an outer part for contacting a breast of a user in a mouth section of the breast receiving funnel, and an inner part extending from a portion of the outer part into a first side of a throat section of the breast receiving funnel,
   wherein the elongate inflatable bladder is configured to fit in a teat receiving space in a second side of the throat of said breast receiving funnel so that the bladder extends from the second side of the throat of said funnel towards the mouth of said funnel, and lies between a user's teat and the funnel at the second side of the throat when the breast is inserted in said funnel, such that the elongate inflatable bladder is configured to deform towards a user' teat located in the teat receiving space in a predetermined manner when a pressure difference is applied between the teat receiving space and the pressures chamber such that a peristaltic action is applied to said user's teat, to aid the expression of milk therefrom,
   wherein the throat section has a cylindrical shape,
   wherein the first side and the second side are equal parts that together form the cylindrical shape, and
   wherein the inner part of the secondary insert portion is arced to continuously cover a majority of the first side of the throat and the elongate inflatable bladder at least partially covers the second side of the throat so that the inner part of the secondary insert portion is diametrically opposite the elongate inflatable bladder in the throat and the first side is devoid of the elongate inflatable bladder, and wherein the secondary insert portion is not inflatable.

2. An insert according to claim 1, wherein the elongate inflatable bladder is formed from a resiliently deformable membrane, and wherein the resiliently deformable membrane is configured to deform towards the user's teat located in the teat receiving space in a predetermined manner when a positive pressure is applied in the elongate inflatable bladder such that a peristaltic action is applied to a user's teat.

3. An insert according to claim 1, wherein the elongate inflatable bladder is formed from a resiliently deformable membrane.

4. An insert according to claim 3, wherein the stiffness of the resiliently deformable membrane varies along the length of the bladder, such that a front stiffness of the resiliently deformable membrane proximate to a front end of said bladder is lower than the stiffness of the resiliently deformable membrane at a distal rear end of said bladder.

5. The insert according to claim 4, wherein the resiliently deformable membrane has a diverging wall thickness which increases away from said front end such that a thinner portion of said membrane proximate to the front end of the bladder deforms towards said user's teat located in said teat receiving space prior to a thicker portion of said membrane proximate to the distal rear end of the bladder deforms towards said user's teat.

6. An insert according to claim 4, wherein the elongate inflatable bladder has a fluid inlet disposed proximate to said distal rear end of the bladder to allow the flow of fluid into and out of the pressure chamber.

7. An insert according to claim 6, wherein the resiliently deformable membrane forms opposing upper and lower membrane walls of the bladder, wherein the lower membrane wall is configured to lie against the funnel and the upper membrane wall is configured to deform towards a user's teat located in the teat receiving space when the insert is disposed in said funnel.

8. A breast receiving funnel for a breast pump comprising an insert wherein the insert comprises:
a primary inset portion having an elongate inflatable bladder which defines a pressure chamber; and
a secondary insert portion having an outer part for contacting a breast of a user in a mouth section of the breast receiving funnel, and an inner part extending from a portion of the outer part into a first side of a throat section of the breast receiving funnel,
wherein the elongate inflatable bladder is configured to fit in a teat receiving space in a second side of the throat of said breast receiving funnel so that the bladder extends from the second side of the throat of said funnel towards the mouth section of said funnel, and lies between a user's teat and the funnel at the second side of the throat when the breast is inserted in said funnel, such that the elongate inflatable bladder is configured to deform towards a user's teat located in the teat receiving space in a predetermined manner when a pressure difference is applied between the teat receiving space and the pressure chamber such that a peristaltic action is applied to said user's teat, to aid the expression of milk therefrom,
wherein the throat section had a cylindrical shape,
wherein the first side and the second side are equal parts that together form the cylindrical shape, and
wherein the inner part of the secondary insert portion is arced to continuously cover a majority of the first side of the throat and the elongate inflatable bladder at least partially covers the second side of the throat so that the inner part of the secondary insert portion is diametrically opposite the elongate inflatable bladder in the throat and the first side is devoid of the elongate inflatable bladder, and wherein the secondary insert portion is not inflatable.

9. A breast receiving funnel according to claim 8, further comprising a rigid outer shell with a funnel opening for receiving a user's teat therethrough, wherein the insert locates against the rigid shell.

10. A breast receiving funnel according to claim 9, wherein the rigid outer shell comprises a planer inner surface and the insert locates against said planar inner surface.

11. A breast receiving funnel according to claim 9, wherein a rear end of the bladder is disposed distal to the funnel opening and a front end of the bladder is disposed proximate to the funnel opening, and wherein the rear end of the bladder is mounted in the funnel such that the front end of the bladder is not constrained.

12. A breast receiving funnel according to claim 11, wherein the mouth section includes an opening to the funnel and the throat section connecting the mouth section to a main body of a breast pump, wherein the bladder is disposed in the throat section, and the front end of the bladder extends into the mouth section.

13. A breast receiving funnel according to claim 12, wherein the secondary insert has a circumferentially extending resiliently deformable wall disposed in the mouth section and extends over the front end of the bladder such that said front end does not contact a user's teat when a user's teat is disposed in said funnel.

\* \* \* \* \*